United States Patent [19]

Kamiya et al.

[11] Patent Number: 4,699,509
[45] Date of Patent: Oct. 13, 1987

[54] DEVICE FOR MEASURING CONTAMINATION OF LUBRICANT

[75] Inventors: Sigeru Kamiya, Chiryu; Masaei Nozawa, Aichi; Toshinobu Ishida; Hideaki Sasaya, both of Okazaki, all of Japan

[73] Assignee: Nippon Soken, Inc., Nishio, Japan

[21] Appl. No.: 724,962

[22] Filed: Apr. 19, 1985

[30] Foreign Application Priority Data

Apr. 21, 1984 [JP] Japan .................................. 59-79345
Mar. 20, 1985 [JP] Japan .................................. 60-57288

[51] Int. Cl.$^4$ .......................................... G01N 33/28
[52] U.S. Cl. ...................................... 356/70; 356/436
[58] Field of Search ................. 356/70, 128, 436, 440; 250/576, 577; 340/57, 59

[56] References Cited

U.S. PATENT DOCUMENTS 1,746,616  2/1930  Sounitza ................................. 356/70
4,003,661  1/1977  Yamano ................................. 356/70
4,497,200  2/1985  Tournier ................................ 340/59

FOREIGN PATENT DOCUMENTS 0037934   3/1980   Japan .................................... 356/70
0076938   6/1980   Japan .................................... 356/70
57-98842   6/1982   Japan .
57-182152  11/1982  Japan .
0176651  10/1984   Japan .................................... 356/70
0105962   6/1985   Japan .................................... 356/70

Primary Examiner—Eugene R. LaRoche
Assistant Examiner—David Mis
Attorney, Agent, or Firm—Cushman, Darby & Cushman

[57] ABSTRACT

In a lubricant contamination measuring device, an optical path gap is provided between a light source window at a light source side and a light receiving window at a light receiving element side. A lubricant having an amount of contaminant to be measured in accordance with a light transmittance is present in the optical path gap and the length of the optical path gap is selected to be shorter than a predetermined length. At least one of the light source and light receiving windows has a convex shape, and the center of the convex window is in contact with a surface of the other window. Thus, the amount of contaminant in the lubricant can be measured up to a high contamination range.

11 Claims, 23 Drawing Figures

DEVICE FOR MEASURING CONTAMINATION OF LUBRICANT

BACKGROUND OF THE INVENTION

1. Field of the Invention

The present invention relates to a device for measuring the amount of a contaminant in a lubricant. The device according to the present invention is used, for example, to measure a concentration of carbon particles contained in a lubricant of an internal combustion engine of a vehicle, in particular, a diesel engine.

2. Description of the Related Art

Various contaminants such as fine sand particles contained in engine intake air and oxides produced by combustion of fuel and the like are introduced into an engine lubricant in accordance with an engine operating time. Particularly, in a diesel engine, it is known that a large number of carbon particles contained in the exhaust gas are introduced into and contaminate the lubricant. Since the carbon particles introduced into the lubricant accelerate wear of respective sliding portions of the engine, when the concentration of the carbon particles increases beyond a certain limit, the lubricant must be replaced.

A method for measuring the concentration of the carbon particles is known wherein a portion of the lubricant is sampled from the engine and passed through a filter, and the weight of particles collected on the filter is measured or the collected particles are centrifuged and weighed. However, with this method, the concentration of the carbon particles cannot be measured when the engine is driven, and any changes over a period of time cannot be measured.

Another conventional lubricant contamination measuring device disclosed in, for example, Japanese Unexamined Patent Publication (Kokai) No. 57-98842, is provided with a light source and a photo cell at two end portions of a lubricant reservoir so that the amount of light received by the photo cell is decreased in accordance with the amount of contaminant in the lubricant.

In such a device, when the distance between the light source and the light receiving element is relatively far apart, the concentration of the carbon particles in the lubricant cannot be measured, for the following reasons. A decrease in a light transmittance due to the introduction of carbon particles in the lubricant can be expressed in the following equation in accordance with various experiments conducted. That is, when a light transmittance of the contaminated lubricant with respect to a noncontaminated lubricant is given by T, a distance between the light source and the light receiving element, more specifically, an optical path length in the lubricant, is given by D (mm), and a coefficient is given by K, a carbon weight concentration $\alpha$ (%) can be expressed by $\alpha = 1/(K \cdot D) \cdot \log(1/T)$. The coefficient K is about 17.4 (1/mm). From the above equation, the light transmittance T with respect to the carbon weight concentration is expressed by $T = 10^{-K \cdot D \cdot \alpha}$.

The light transmittance with respect to the carbon concentration changes significantly in accordance with a change in the optical path length D. When the optical path length D is 1 mm, the concentration $\alpha$ is about 0.2%, and the light can hardly pass through the lubricant, more specifically, $T = 3.3 \times 10^{-4}$. The transmitted light is converted into an electric signal by the light receiving element opposing the light source to drive an indicator such as a concentration indicator. However, in a general electric signal processing circuit, the lower limit of a signal magnitude ratio for processing signals is about 1:1000. Therefore, as described above, when the optical path length D = 1 mm, since the transmittance T of the light reaches 0.001 at the carbon concentration of 0.172%, the signal becomes too weak in practice when the concentration exceeds this value, and therefore, a concentration measurement cannot be performed.

When the optical path length is set to be short, a transmittance curve is approximately a straight line, and the range in which a concentration measurement can be performed can be widened. Although the required range of concentration measurement differs in accordance with the type of engine, an upper limit of the concentration $\alpha$ is generally about 0.5% to 4%. For example, when a concentration $\alpha$ of up to 0.5% is to be measured, the optical path length D satisfying T = 0.001 for $\alpha = 0.5\%$ is 0.034 mm. Similarly, when a concentration $\alpha$ of up to 4% is to be measured, the optical path length D satisfying the same condition becomes 0.043 mm. As described above, when the carbon concentration in the lubricant is measured using light transmittance, the optical path length is an important factor. In practice, unless the optical path length is 0.34 mm or less, the necessary range of concentration cannot be measured. Thus, the optical path length must be set to be 0.34 mm or less.

To widen the range of concentration measurement, as described above, the optical path length D must be made very much shorter. However, in this case, the following problems occur. First, a variation in the measurement due to the optical path length occurs. This is because when an optical path gap (defining the optical path length) changes slightly by, e.g., several tens of micrometers, the relationship between the carbon concentration and the light transmittance is widely varied. That is, the optical path gap must be precisely defined. Second, when the optical path gap is shortened as described above, the rate of replacement of the lubricant between the light source and the light receiving element is low. For example, when the contaminated lubricant is replaced with new lubricant, a new concentration value cannot be quickly indicated. Furthermore, agglomerated contaminant particles can easily clog the optical path gap.

SUMMARY OF THE INVENTION

It is an object of the present invention to precisely measure contamination in a lubricant or an amount of contaminant in a lubricant up to a high contamination range by setting an optical path gap length between a light source and light receiving elements to a predetermined length or less, forming at least one of the light source and light receiving elements into a convex shape, and arranging the convex shape formed surface to abut against the surface of the opposite window.

According to the fundamental aspect of the present invention, a device is provided for measuring contamination of a lubricant, in which an optical path gap is provided between a light source window provided at a light source side and a light receiving window provided at a light receiving element side in such a manner that the lubricant in which contamination is to be measured in accordance with a transmittance of light can be present in the optical path gap, and the length of the optical path gap is selected to be less than 0.34 mm.

According to another aspect of the present invention, a device is provided for measuring contamination of a lubricant, in which an optical path gap is provided between a light source window provided at a light source side and a light receiving window provided at a light receiving element side in such a manner that at least one of the light source and light receiving windows has a convex surface, the lubricant in which contamination is to be measured in accordance with a transmittance of light can be present in the optical path gap, and the center of the convex surface of the window is in contact with a surface of the other window.

According to another aspect of the present invention, a device is provided for measuring contamination of a lubricant. The device comprises a measuring unit, dipped in an engine lubricant, for detecting an amount of contaminant in a lubricant; a temperature detecting unit for detecting a lubricant temperature, a controlling unit for generating a control signal in response to a signal from the measuring unit and the temperature detecting unit; and a signaling unit for signaling a level of contamination in response to the control signal. The controlling unit operates the signaling unit when the temperature detecting unit detects that the lubricant temperature has reached a predetermined temperature.

DESCRIPTION OF THE PREFERRED EMBODIMENTS

Figure 3:
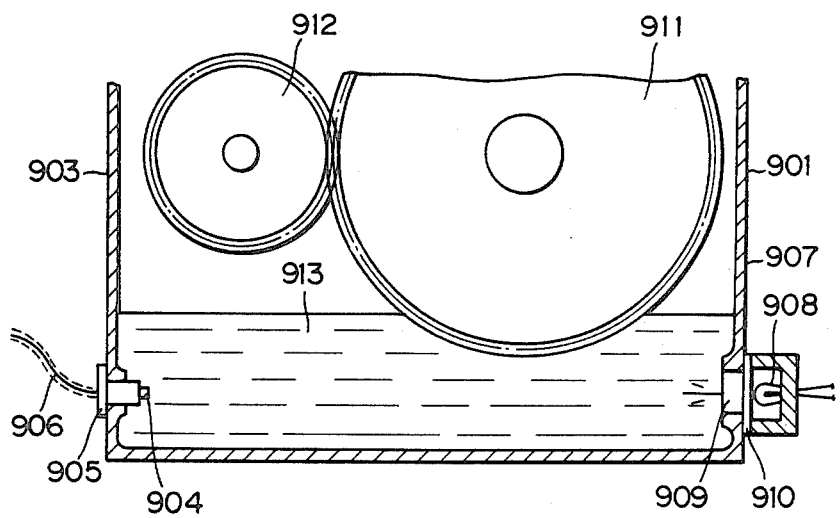
FIG. 3 is a view showing a conventional lubricant contamination measuring device.

Prior to the description of preferred embodiments of the present invention, a conventional lubricant contamination measuring device will first be described with reference to FIG. 3. The conventional device is provided with a light source 908 and a photo cell 904 at two end portions of a lubricant reservoir 901 so that the amount of light received by the photo cell 904 is decreased in accordance with the amount of contaminant in the lubricant 913. Referring to FIG. 3, reference numeral 905 denotes a sensor; 906, a power supply cable; 903 and 907, side walls; 909, a mount hole; 910, a transparent plate; and 911 and 912, gears (see Japanese Unexamined Patent Publication (Kokai) No. 57-98842).

In such a device, when the distance between the light source and a light receiving element is long, the concentration of the carbon particles in the lubricant cannot be measured, for the reason described below. A decrease in a light transmittance due to the introduction of the carbon particles in the lubricant can be expressed by the following equation. That is, when a light transmittance of the contaminated lubricant with respect to a noncontaminated lubricant is given by T, a distance between the light source and the light receiving element, more specifically, an optical path length in the lubricant, is given by D (mm), and a coefficient is given by K, a carbon weight concentration $\alpha$ (%) can be expressed by:

$$\alpha = 1/(K \cdot D) \cdot \log(1/T) \ldots \quad (1)$$

The coefficient K is about 17.4 (1/mm). From equation (1), the light transmittance T with respect to the carbon weight concentration is expressed as follows:

$$T = 10^{-K \cdot D \cdot \alpha} \ldots \quad (2)$$

Figure 4:
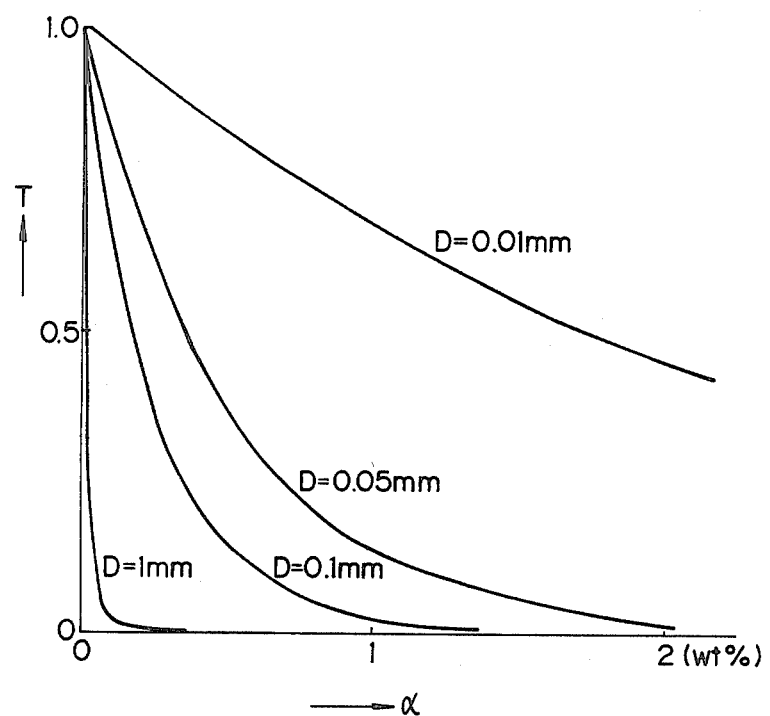
FIGS. 4 and 5 are respectively graphs for explaining contamination measurement characteristics.

FIG. 4 shows the relationship between the carbon weight concentration (abscissa) and the transmittance (ordinate) expressed by equation (2). As can be seen from FIG. 4, the light transmittance with respect to the carbon concentration changes in accordance with a change in the optical path length D. When the optical path length D is 1 mm and the concentration $\alpha$ is about 0.2%, the light can hardly pass through the lubricant, more specifically, $T = 3.3 \times 10^{-4}$. The transmitted light is converted into an electric signal by the light receiving element opposing the light source, to drive an indicator such as a concentration indicator. However, in a general electric signal processing circuit, the lower limit of a signal magnitude ratio for processing signals is about 1:1000. Therefore, as described above, when the optical path length D = 1 mm, since the transmittance T of the light reaches 0.001 at the carbon concentration of 0.172%, the signal becomes too weak in practice when the concentration exceeds this value, and concentration measurement cannot be performed.

FIG. 4 also shows transmittance curves when the optical path length D is set to be 0.1 mm, 0.05 mm, and 0.01 mm. As apparent from FIG. 4, when the optical path length is set to be short, the transmittance curve approaches a straight line, and a concentration measurement range in which measurement can be performed can be widened. Although the required range of concentration measurement differs in accordance with the type of engine, the upper limit of the concentration $\alpha$ is generally about 0.5% to 4%. For example, when measurement is to be performed for a concentration α of up to 0.5%, the optical path length D satisfying T=0.001 for α=0.5% is 0.034 mm. Similarly, when measurement is to be performed for a concentration α of up to 4%, the optical path length D satisfying the same condition becomes 0.043 mm. As described above, when the carbon concentration in the lubricant is measured by light transmittance, the optical path length is an important factor. In practice, unless the optical path length is 0.34 mm or less, the needed concentration range cannot be measured. Thus, the optical path length must be set to be 0.34 mm or less.

Figure 5:
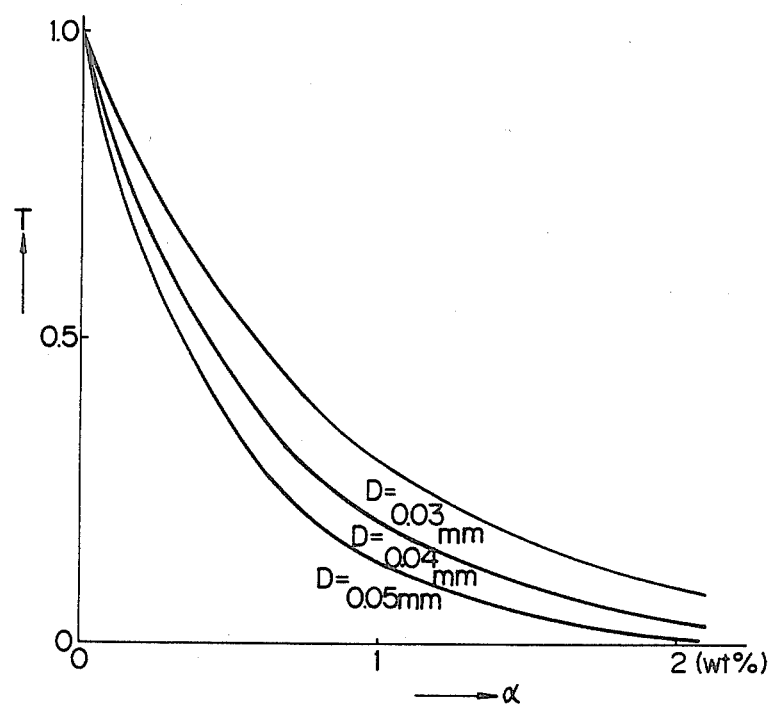

In order to widen the measurement range of the concentration, as described above, the optical path length D must be made much shorter. However, in this case, the following problems occur. First, a variation in the measurement due to the optical path length occurs. FIG. 5 shows changes in the light transmittance when the optical path length D (optical path gap) is changed from 0.05 mm to 0.04 mm and 0.03 mm. As can be seen from FIG. 5, when an optical path gap changes slightly by, e.g., several tens of micrometers, the relationship between the carbon concentration and the transmittance varies widely. That is, the optical path gap must be precisely defined. Second, when the optical path gap is shortened as described above, the rate of lubricant replacement between the light source and the light receiving element is low. For example, when the contaminated lubricant is replaced with new lubricant, a new concentration value cannot be quickly indicated. Furthermore, agglomerated contaminant particles can easily clog the optical path gap.

Figure 1:
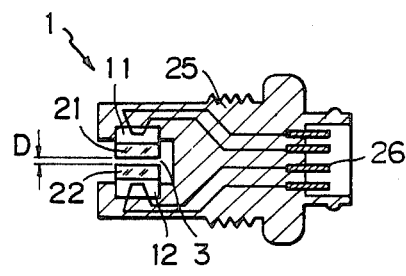
FIG. 1 is a view showing an embodiment of a lubricant contamination measuring device according to a first aspect of the present invention.

FIG. 1 shows an embodiment of a lubricant contamination measuring device according to the first aspect of the present invention. In the device shown in FIG. 1, reference numeral 11 denotes a light source such as a light emitting diode; 12, a light receiving element such as a photodiode or phototransistor; and 21 and 22, windows made of glass or transparent synthetic resin. The light source 11 and the light receiving element 12 constitute a sensor 1. An optical path gap 3 is provided between the opposing surfaces of the windows 21 and 22. In the device shown in FIG. 1, a distance D of the gap 3 is set to be 0.34 mm or less. Reference numeral 25 denotes a body made of a resin and/or a metal. The body holds the light source and the light receiving element at given positions on an oil reservoir of an engine or the like. Reference numeral 26 denotes terminal portions for connecting the light source and the light receiving element to signal processing and display units (not shown). As described above, the relationship between the optical path gap 3 and the concentration of the carbon particles in the lubricant is as follows: when D=0.34 mm, the concentration can be measured up to 0.5%, when D=0.1 mm, it can be measured up to 1.7%, and when D=0.05 mm, the concentration can be measured up to 3.4%.

Figure 2:
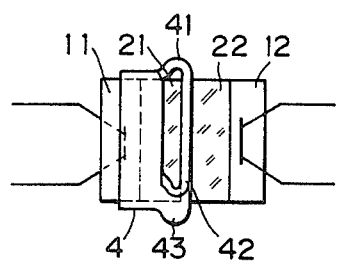
FIG. 2 is a view showing another embodiment of a lubricant contamination measuring device according to the first aspect of the present invention.

In this case, a distance D of the optical path gap 3 must be precisely defined, and an example of an arrangement for realizing this is shown in FIG. 2. Referring to FIG. 2, reference numeral 4 denotes a substantially cylindrical spacer ring. The spacer ring 4 has substantially U-shaped projections on its periphery, indicated by numerals 41, 42, and 43. When the projections are inserted between the windows 21 and 22, the optical path gap can be precisely defined by a thickness of the projections 41, 42, and 43.

Figure 6:
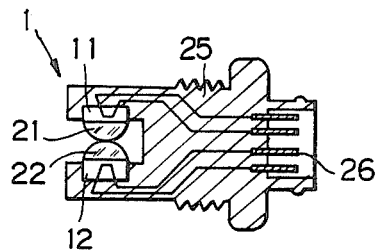
FIG. 6 is a view showing an embodiment of a lubricant contamination measuring device according to a second aspect of the present invention.

FIG. 6 shows an embodiment of a lubricant contamination measuring device according to the second aspect of the present invention. The same reference numerals as in FIG. 4 denote the same parts in FIG. 6. In the device shown in FIG. 1, although the opposing surface of the windows 21 and 22 are flat, in the device shown in FIG. 6, the windows are formed into a semispherical shape and are brought into contact with each other. A radius of the semispherical surface is about 1 to 3 mm. With the above arrangement, the optical gap can vary from substantially zero to several millimeters, and a sufficiently high output voltage can be maintained even when a high concentration must be measured.

Figure 7:
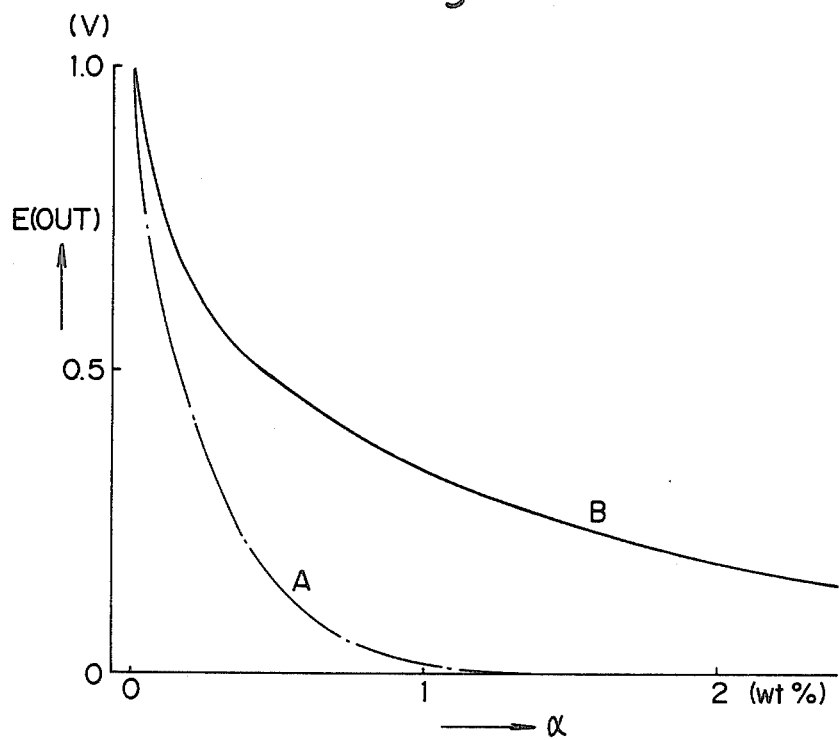
FIG. 7 is a graph showing characteristics of the device shown in FIG. 6.

FIG. 7 shows characteristics of the device shown in FIG. 6. Referring to FIG. 7, the abscissa indicates the carbon weight concentration α (%) and the ordinate indicates an output voltage E(out) (V) of the light receiving element. In FIG. 7, curve A represents the case wherein the optical path gap is 0.1 mm in the device of FIG. 1, and curve B represents the case wherein a radius of the semispherical surface is 2.5 mm in the device of FIG. 6. As apparent from FIG. 7, the output voltage E(out) does not abruptly change at the high concentration side in the device shown in FIG. 6, and measurement can be performed in a wide concentration range. In the device shown in FIG. 6, since the optical path gap formed by placing the two semispherical surfaces in contact is utilized, the gap requires no adjustment when assembled. In addition, since the lubricant flow in the gap portion is smooth, the response time with respect to a change in concentration can be shortened. Furthermore, in the embodiment of the second aspect of the present invention, the presence or absence of the lubricant can be detected in addition to the carbon concentration. This aspect will be described with reference to FIGS. 8 and 9.

Figure 8:
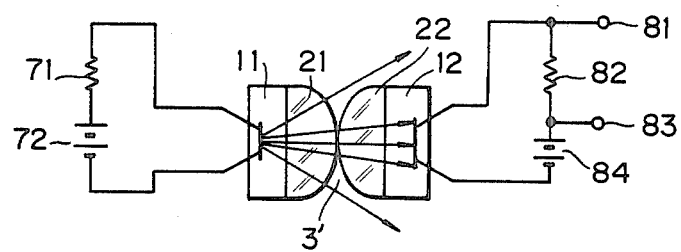
FIGS. 8 and 9 are respectively views for explaining an operation of the device shown in FIG. 6.
Figure 9:
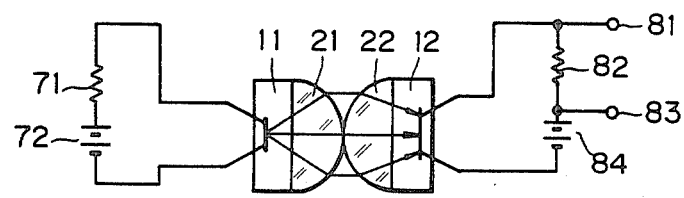

FIG. 8 shows the optical path from the light source to the light receiving element when the lubricant is present. In this case, since a refractive index of the windows 21 and 22 mainly made of glass is substantially the same as that of the lubricant, the light enters on a straight plane irrespective of the convex shape of the windows 21 and 22. For this reason, light components largely shifted from the optical axis connecting the light source 11 and the light receiving element 12 cannot reach the light receiving element 12. FIG. 9 shows the optical path when the lubricant is absent. Most of light emitted from the light source can reach the light receiving element 12 due to a lens function of the windows 21 and 22, and the light amount received by the light receiving element is greatly increased compared to when the lubricant is present. In other words, the presence or absence of the lubricant can be detected.

Note that reference numerals 72 and 84 denote power supplies for driving the light source and light receiving element; 71, a stabilizing resistor; and 82, a resistor for detecting a current flowing through the light receiving element so as to generate a voltage proportional to the received light amount between terminals 81 and 83 connected to its two ends. The voltage is converted to correspond to the carbon concentration by a conventional process of an electric circuit, thus driving a display device or the like.

Figure 10:
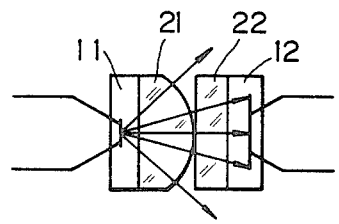
FIGS. 10, 11, 12, 13A, 13B, and 13C are respectively views showing another embodiment of a lubricant contamination measuring device according to the second aspect of the present invention.

FIG. 10 shows an example in which one of the windows is semispherical, and the other window is flat. The same effect as in FIGS. 8 and 9 can be obtained.

Figure 11:
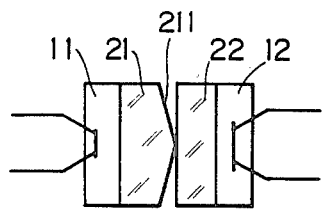
Figure 12:
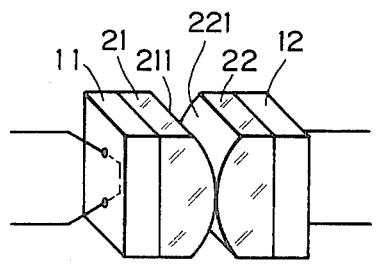

FIG. 11 shows an example wherein one of the windows is conical. Referring to FIG. 11, a surface 211 of the window opposing the window 22 is formed into a conical shape. FIG. 12 shows a case wherein the window is semicylindrical. Substantially the same effect as in the case wherein the window is formed into a conical shape can be obtained.

In the embodiments described above, the light emitting diode as the light source and the photodiode as the light receiving element are dipped in the lubricant. On the other hand, since the temperature of the lubricant is increased to about 120° C. when the engine is driven, an error in a measurement value may occur in accordance with the temperature characteristics of the respective elements.

Figure 13A:
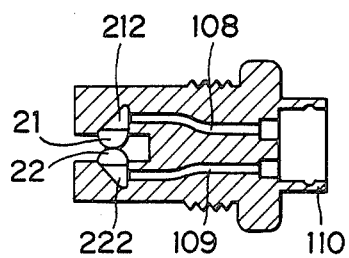
Figure 13B:
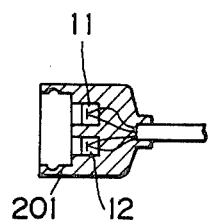
Figure 13C:
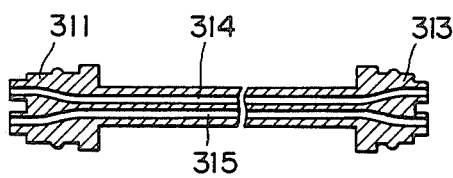

To prevent this, FIGS. 13A, 13B, and 13C show examples wherein the respective elements are not dipped in the lubricant. FIG. 13A shows a detector unit dipped in the lubricant. The detector unit comprises windows 21 and 22 for forming an optical gap, light guides 108 and 109, formed of an optical fiber, for guiding external light to the window, and prisms 212 and 222 for deflecting light 90°.

FIG. 13B shows a light emitting/receiving element unit in which a light emitting diode 11 and a photodiode 12 are built in. FIG. 13C shows a cable connecting the detector unit shown in FIG. 13A and the light emitting-/receiving element unit shown in FIG. 13B, which comprises light guides 314 and 315 having connectors 311 and 313 connected to connectors 110 and 201, respectively. With the above arrangement, since the light emitting/receiving element unit can be placed on a portion of the reservoir having a relatively low temperature, the influence of temperature can be abated.

Figure 14:
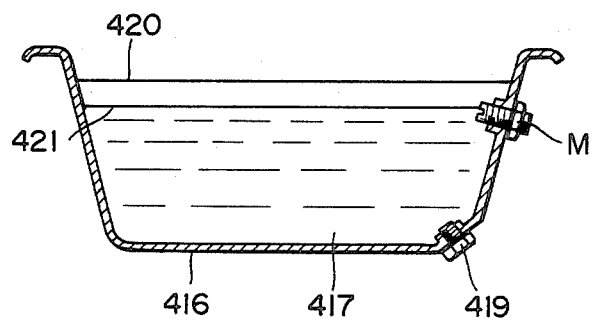
FIG. 14 is a view showing an arrangement when the lubricant contamination measuring device according to the embodiment of the present invention is mounted on an engine.

FIG. 14 shows an arrangement when the device of FIG. 4 is mounted on an engine. Reference numeral 416 denotes an oil pan of the engine; 417, a lubricant; M, a measurement device; and 419, a drain plug. Reference numeral 420 denotes a lubricant level in a normal state; and 421, a lubricant level when a lubricant amount is at its lower limit. When the measuring device is fixed at a position corresponding to the lower limit of the lubricant level, detection of the lubricant amount can be also performed. Note that the measuring device shown in FIG. 4 can be mounted at a distal end of a level gauge generally used for monitoring the lubricant amount.

Figure 15:
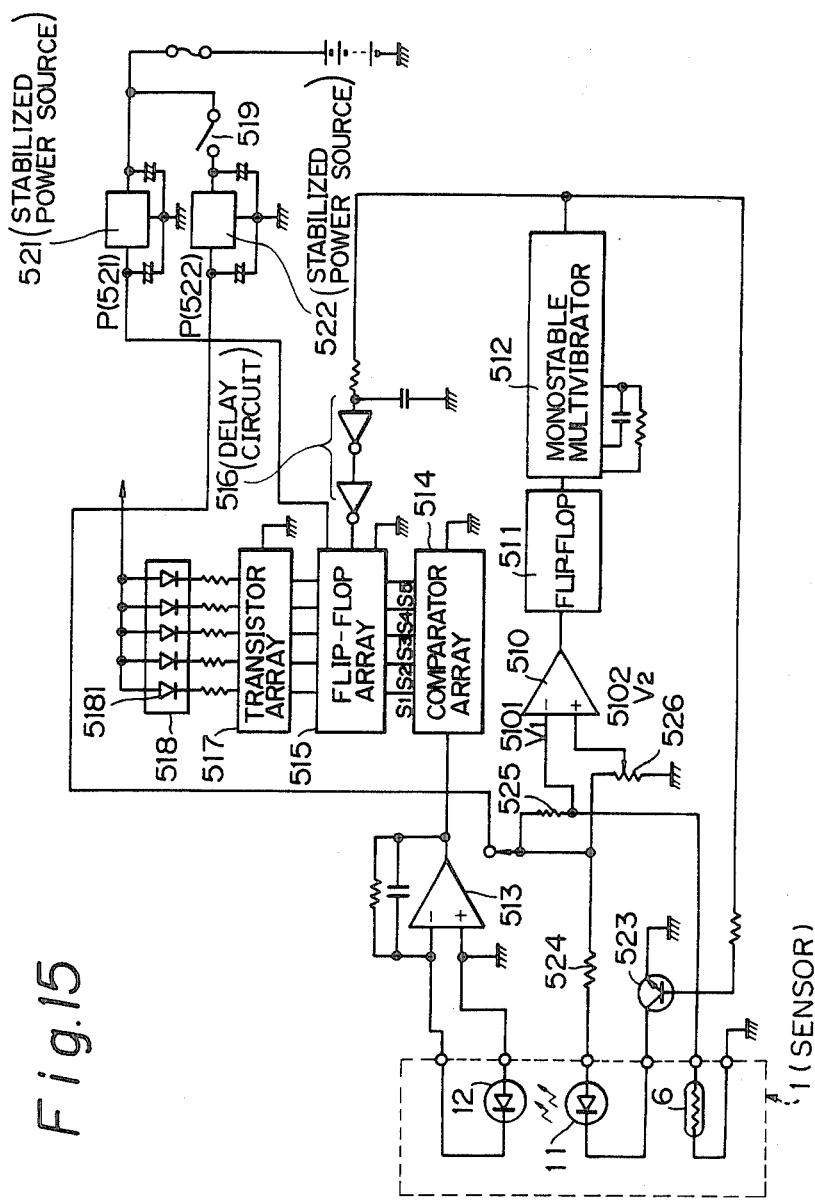
FIG. 15 is a block diagram of a lubricant contamination measuring device including a unit which removes any influence from a temperature according to an embodiment of the present invention.

FIG. 15 shows a lubricant contamination detecting device including a unit for removing the influence of a temperature according to an embodiment of the present invention. Referring to FIG. 15, a voltage is applied to a thermistor 6 from a node P(522) through a resistor 525. A terminal voltage V(5101) of the thermistor 6 is applied to one input terminal of a comparator 510. A voltage corresponding to a preset temperature is generated by a voltage divider 526 and is applied to the other input terminal of the comparator 510. When the lubricant temperature is increased, the resistance of the thermistor 6 is decreased and the voltage V(5101) is gradually decreased until it reaches a level corresponding to the preset temperature (preferably, about 50° C. to 60° C.). When the voltage V(5101) becomes lower than the reference voltage V(5102), the output from the comparator 510 is changed stepwise from LOW level to HIGH level. The output from a flip-flop 511 is inverted by the HIGH level signal and the inverted signal is applied to a monostable multivibrator 512. The monostable multivibrator 512 generates a single pulse signal having a pulse width of about 1 sec, and transistor 523 is turned ON in response to this pulse signal. Thus, a current flows in the light-emitting diode 11 through the load resistor 524, causing it to emit light.

As described above, in the device shown in FIG. 15, the thermistor 6 as the temperature detecting means is arranged so that the light-emitting diode 11 is turned on when the lubricant temperature reaches a predetermined value.

The photodiode 12 generates a photocurrent in accordance with the amount of the contaminant in the lubricant. The photocurrent is converted into voltage by an amplifier 513 and the voltage is applied to a comparator array 514. The comparator array 514 sends HIGH level signals to some of the output signal lines S1 to S5 thereof in accordance with the output voltage from the amplifier 513. These HIGH level signals are supplied to a flip-flop array 515 and stored therein in response to the pulse signal generated from the monostable multivibrator 512, which is delayed by a delay circuit 516 by a given time from the beginning of light emission by the light-emitting diode 11. In accordance with the stored signals, some of the light-emitting diodes 5181 to 5185 of a light-emitting diode array 518 are turned on, thereby indicating an output signal level of the amplifier 513, i.e., the level of contamination of the lubricant. Power is supplied to the flip-flop array 515 through a node P(521) from a stabilized power source 521. Since power is continuously supplied to the flip-flop array 515 from the stabilized power source 521 connected to a power source 520 and not through the ignition switch 519, the flip-flop array 515 can store signals after the engine is stopped. Power for operating elements other than the flip-flop array 515 is supplied through the node P(522) from a stabilized power source 522 connected to the power source 520 through the ignition switch 519. For this reason, when the engine is started, the light-emitting diode array 518 indicates a previous measurement value in accordance with signals stored in the flip-flop array 515, and simultaneously the flip-flop 511 is cleared and waits to receive a signal from the comparator 510.

Figure 16:
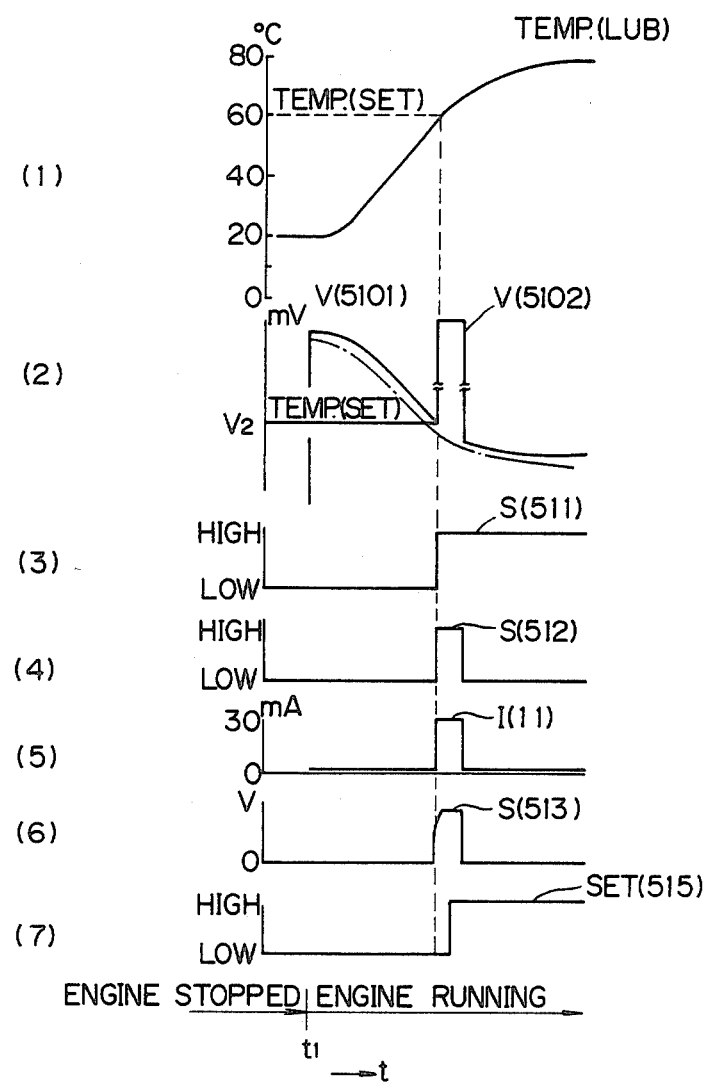
FIG. 16 is a waveform chart showing a signal waveform in the device shown in FIG. 15.

Operation of the control circuit having the above arrangement will be described with reference to a waveform chart shown in FIG. 16. Referring to FIG. 16, the axis of abscissa represents the elapse of time t, and point $t_1$ represents an engine starting point. The axis of the ordinate of the waveform chart represents, (1), an engine lubricant temperature TEMP(LUB); (2), an input voltage V(5101) of the comparator 510; and (3) to (7), outputs of respective components of the control circuit.

When the engine is started, the lubricant temperature TEMP(LUB) is increased in accordance with the elapse of time t, as illustrated in the waveform chart (1). In response to this, the resistance of the thermistor 6 is decreased, and the voltage V(5101) of the comparator 510 is therefore decreased, as indicated by a curve in the waveform chart (2). When the voltage V (5101) is lower than a reference voltage V(5102), i.e., when the lubricant temperature reaches about 60° C., the output from the comparator 510 goes to HIGH level and the flip-flop 511 also goes to HIGH level, as illustrated in the waveform chart (3). Thus, as in the waveform chart (4), the pulse signal is generated from the monostable multivibrator 512. While the pulse signal is being generated, a drive current flows in the light-emitting diode 11, as in the waveform chart (5), causing the light-emitting diode 11 to emit light. The photodiode 12 detects the light emitted from the diode 11 in accordance with the level of the contamination and generates a photocurrent in accordance therewith. The photocurrent is converted by the amplifier 513 into the voltage corresponding to the level of the contamination as in the waveform chart (6). The voltage is supplied to the comparator array 514, thereby selecting the output signal lines thereof in accordance with the level of the contamination.

When the output from the amplifier 513 is stabilized, a set signal SET(515) of the flip-flop array 515 is generated, as illustrated in the waveform chart (7), and the output level of the comparator array 514 is stored in the flip-flop array 515. In addition, the corresponding light-emitting diodes (5181 to 5185) of the light-emitting diode array 518 are turned on in accordance with the level of the contamination. Since the flip-flop array 515 is powered by the stabilized power source 521 when the engine is stopped, it causes the previous measurement value stored therein to be displayed when the engine is started again.

As described above, in the device shown in FIG. 15, the lubricant temperature reaches a predetermined level only when the light-emitting diode 11 is turned on for a short period of time, to measure an amount of the contaminant in the lubricant, and thereafter the measurement result is displayed and stored. Thus, since measurement is continuously carried out up to a constant temperature, a compensation circuit for compensating for a change in a luminance of the light-emitting diode 11 due to temperature change is not needed. In addition, since the light-emitting diode 11 need not be turned on at a high temperature, its life can be prolonged.

In the above embodiment, the thermistor provided in the sensor 1 is used as a means for detecting the lubricant temperature. Instead of this, a lubricant temperature sensor can be provided on a portion in which the lubricant is circulated and a detection signal supplied therefrom can be used. Since the lubricant temperature and a cooling water temperature have a certain relationship, a signal from a cooling water temperature sensor of the engine can be used. However, in this case, a signal line for connecting the temperature sensor and the lubricant contamination measuring device must be provided.

Figure 17:
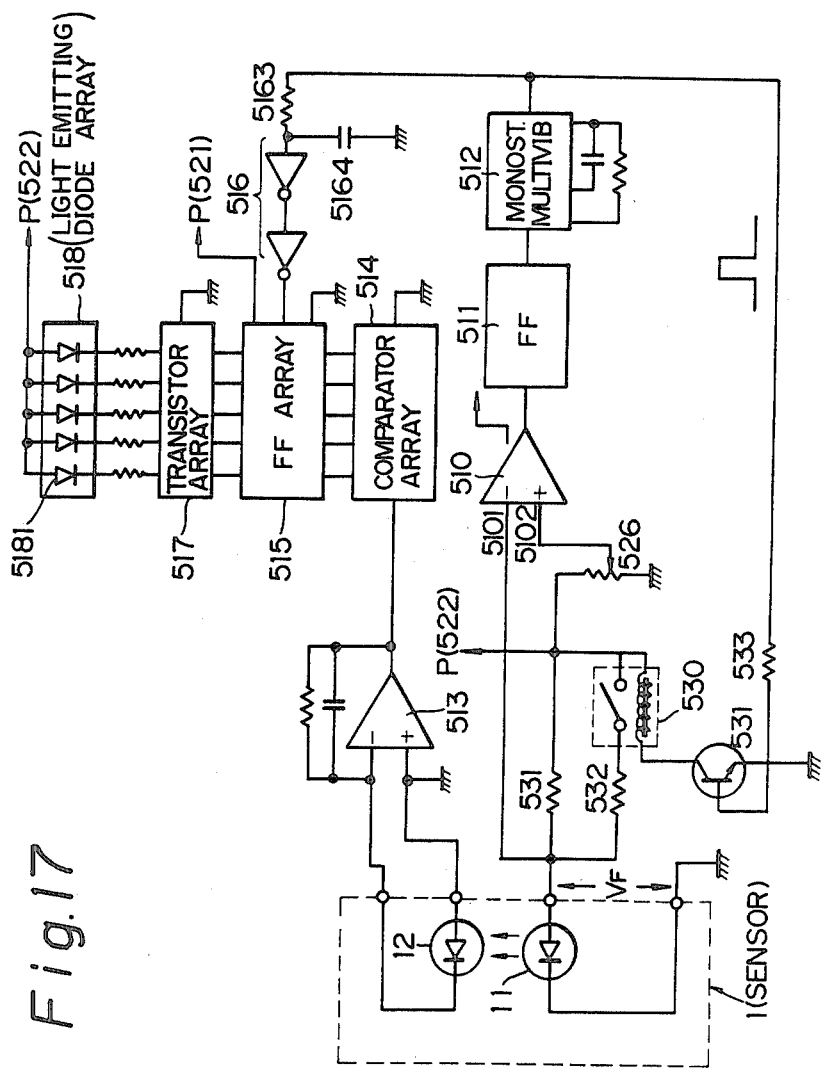
FIGS. 17 and 18 are views respectively showing other embodiments.

FIG. 17 shows a lubricant contamination detecting device including a unit for removing the influence of a temperature according to another embodiment of the present invention. The device shown in FIG. 17 has load resistors having different resistance indicated by reference numerals 531 and 532 for the diode 11, and the resistances of the load resistors can be set at a desired value by a relay 530. In addition, a terminal voltage V(11) of the light-emitting diode 11 is supplied to a temperature detection comparator 510 as an input voltage thereof. In a temperature measurement mode, i.e., when the device is powered, the relay 530 is enabled, and a current of about 1 mA flows in the light-emitting diode 11 through the load resistor 531 of a relatively high resistance, e.g., 5 to 6 kΩ, although this varies due to the power supply voltage. When the lubricant temperature is increased, the terminal voltage V(11) of the light-emitting diode 11, that is, an input voltage V(5101) of the comparator 510, is gradually decreased, as indicated by a curve V(5102) of a waveform chart (2) in FIG. 16. When the input voltage V(5101) drops below a preset voltage V(5102) corresponding to the preset temperature, the output of the comparator 510 is changed stepwise from LOW level to HIGH level, the output of a flip-flop 511 is inverted, and a monostable multivibrator 512 generates a pulse signal of about 1 sec. In response to this signal, a transistor 531 is enabled, and the relay 530 is disabled. Thus, a current flows in the light-emitting diode 11 through the load resistor 532 having a relatively low resistance, and the diode 11 is turned on. When the relay 530 is disabled, a terminal voltage of the light-emitting diode V(12) is increased. When the pulse signal is stopped and the relay 530 is thus enabled, the voltage V(12) is decreased. For this reason, and in response to this, although the comparator 510 generates a signal again, since the flip-flop 511 has been already inverted, the output of the flip-flop 511 is not changed and no pulse signal is generated from the monostable multivibrator 512. It should be noted that the flip-flop 511 is reset when power is supplied by the ignition switch 519. A light-emitting diode array 518 is driven in the same manner as in the above embodiment.

In this manner, the device shown in FIG. 17 does not require the thermistor 6 for detecting the lubricant temperature.

Figure 21:
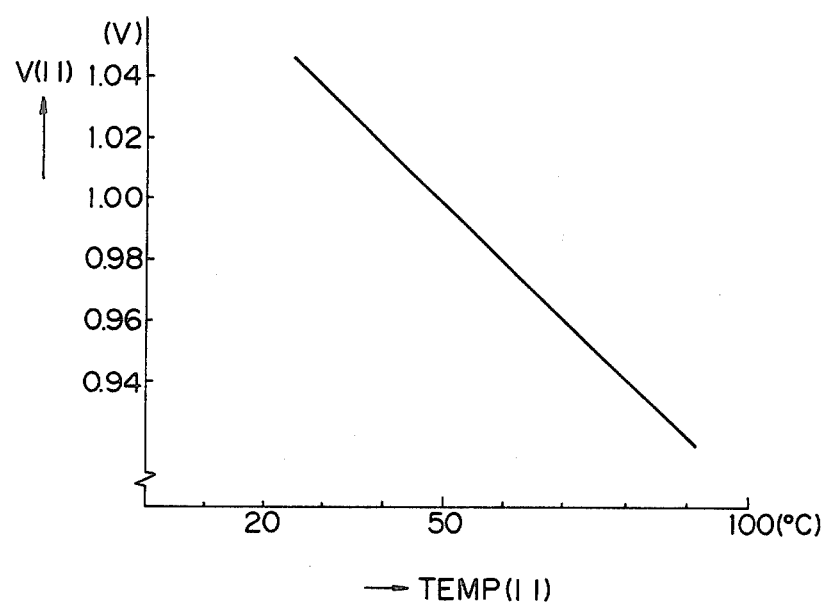
FIG. 21 is a graph showing the relationship between a temperature and a terminal voltage of a light-emitting element.

By utilizing a temperature characteristic of the light emitting diode 11, a special temperature detecting means such as the thermistor 6 can be omitted. When a small current of about 1 mA biases the light-emitting diode 11 in the forward direction, a voltage appearing at the terminal of the light-emitting diode 11 is changed depending upon the temperature thereof, as shown in FIG. 21. When a small current biases the light-emitting diode 11 in the forward direction (generally a diode, but not limited to this), the voltage V(11) at the terminal thereof is decreased in accordance with an increase in the temperature. In the case shown in FIG. 6, a voltage drop of about $-7.4$ mV/° C. is generated. Since the voltage change can closely correspond to the temperature change, the temperature of the element which is approximately equal to the lubricant temperature can be measured by detecting this voltage. Therefore, a specific temperature detecting means is not needed.

Figure 18:
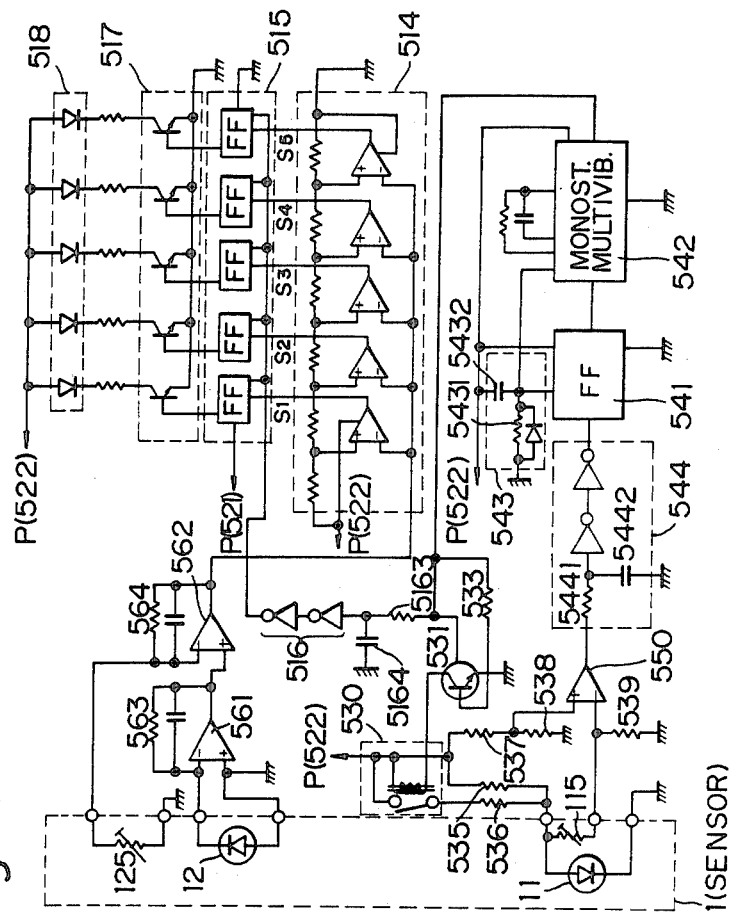

FIG. 18 shows a lubricant contamination detecting device including a unit for removing an influence of a temperature according to still another embodiment of the present invention.

When the light-emitting diode 11 is used in the sensor, a luminance and a temperature dependency of the terminal voltage of the diode 11 when a small current flows therethrough vary widely in accordance with each element (light-emitting diode). Therefore, during manufacturing, a device is required to ensure that the respective sensors are compatible. In the device shown in FIG. 18, a sensor having compatible elements and a display unit are used. The sensor is provided with a variable resistor 115. The terminal voltage of the light-emitting diode 11 is divided by resistors 115 and 539 and the divided voltage is supplied to one input terminal of a comparator 550. With this arrangement, when the variable resistor 115 connected to each light-emitting diode 11 is adjusted, the terminal voltage thereof with respect to a temperature of each sensor can be identical, thereby providing compatibility between the respective sensors.

Figure 19:
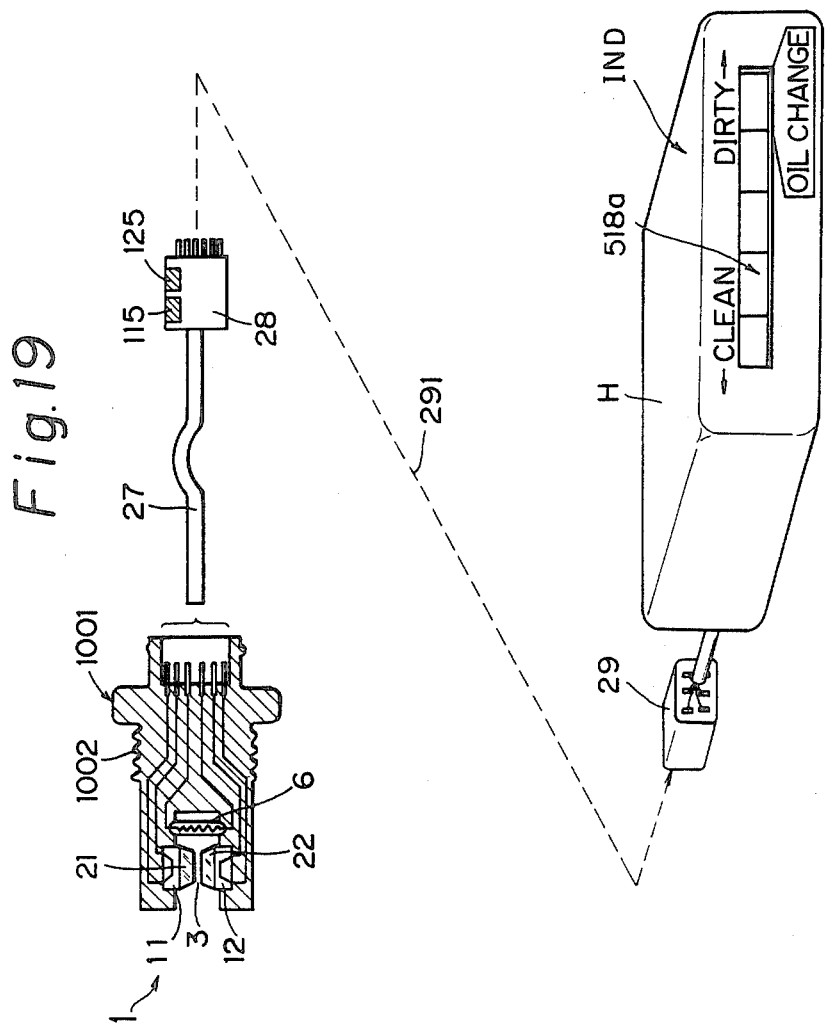
FIG. 19 is a view showing a detailed arrangement of the device shown in FIG. 15.

The luminance of the light-emitting diode 11 and the sensitivity of the photodiode 12 vary widely in accordance with each element, and adjustment of these characteristics is also needed. In order to adjust a variation in a sensor output, a variable resistor 125 is provided. The resistors 125 and 115 are mounted, for example, on a connector 28, as shown in FIG. 19. A photocurrent flowing through the photodiode 12 is amplified by an amplifier 561 and is converted into a voltage. The converted voltage is further amplified by an amplifier 582 and thereafter is supplied to a comparator array 514. The gain of the amplifier 562 is determined by a ratio of the resistances of resistors 564 and 125. Therefore, when the resistance of the resistor 125 is adjusted, a final output of the sensor can be adjusted. Since the resistor 125 is included in the sensor, when the sensor is replaced, the resistor 125 is replaced at the same time. Thus, a sensor including a resistor of an optimum resistance is always used, also resulting in compatibility between respective sensors.

The circuit shown in FIG. 18 comprises a reset circuit 543 and a waveform shaping circuit 544. A flip-flop 541 and a monostable multivibrator 542 are reset by a reset circuit 543 when the ignition switch 519 is turned on. An output waveform of the comparator 550 is shaped by the waveform shaping circuit 544 and is supplied to the flip-flop 541. In the device shown in FIG. 18, since the resistor 115 for adjusting a detection temperature and the resistor 125 for adjusting sensitivity are included in the sensor, detection of the lubricant temperature and sensitivity to the contaminant can be identical in all sensors, thus providing compatibility thereto.

FIG. 19 shows a detailed arrangement of a device shown in FIG. 15. Referring to FIG. 19, a contamination sensor 1 is provided with a light-emitting diode 11 and a photodiode 12. A threaded portion 1002 is formed in a body 1001 of the sensor 1 and the body 1001 is screwed into an oil exhaust port of an oil pan for storing a lubricant of a vehicle engine. Reference numeral 27 denotes a cord for supplying power to the light-emitting diode 11 and for receiving an output voltage from the photodiode 12. A connector 28 is provided at the other end of the cord 27. When the sensor 1 is mounted on the oil pan, the connector 28 is located in an engine compartment.

An indicator unit IND for signaling an amount of a contaminant in the lubricant detected by the sensor 1 is provided at a position which is easily visible from a driver's seat. An indicator section 518a for indicating an amount of the contaminant in the lubricant in five steps is provided on a side surface of a housing H for storing a control circuit. The indicator section 518a comprises five light-emitting diodes 5181 to 5185. In accordance with an increase in the amount of the contaminant, the light-emitting diodes 5181 to 5185 are sequentially turned on from the left to the right, one by one. Thus, when the rightmost diode is turned on, the driver is notified that the lubricant should be replaced. The control circuit in the housing H is connected to the sensor 1 through a connector 29. In this case, the connectors 28 and 29 are connected by a connecting cord 291 (not shown) extending through a front console located between the engine compartment and the passenger compartment.

In the sensor 1, the light-emitting diode 11 and the photo diode 12 are respectively covered with glass windows 21 and 22. The glass windows 21 and 22 oppose each other and are spaced by a predetermined gap 3 which is filled with a lubricant to be measured.

Figure 20:
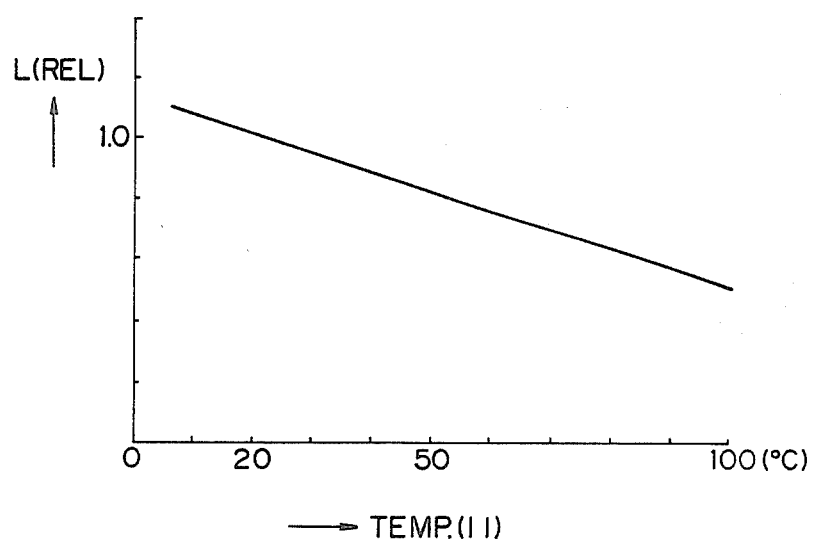
FIG. 20 is a graph showing the relationship between a temperature and a relative luminance of a light-emitting element.

A principle of the device shown in FIG. 15 will be described with reference to FIG. 20.

An amount of the contaminant in the lubricant and the transmittance of light have a certain relationship. When contamination is increased, transmittance is decreased, and therefore an amount of light reaching the light-receiving element is decreased. When this light amount is measured by the light-receiving element, the amount of the contaminant in the lubricant can be measured. However, the temperature of the light-emitting diode 11 is changed in accordance with a change in the lubricant temperature. When the luminance of the light-emitting diode 11 is changed, as shown in FIG. 20, this results in a change in the amount of light reaching the photodiode 2, and the amount of the contaminant of the lubricant cannot be precisely measured. Referring to FIG. 20, the axis of the abscissa represents a temperature TEMP(11) (° C.), and the axis of the ordinate represents a relative luminance L(REL) of a light-emitting diode. In the device shown in FIG. 15, in order to overcome this drawback, the lubricant temperature is measured by the thermistor 6 as a detecting means so that measurement is performed when the lubricant temperature reaches a preset value. The thermistor 6 is arranged in the vicinity of the light-emitting diode 11 and measures the lubricant temperature, i.e., the temperature of the light-emitting diode 11.

We claim:

1. A device for measuring contamination of a lubricant, comprising:

measuring means, dipped in said lubricant, for detecting an amount of contaminant in said lubricant, said measuring means having an optical path gap provided between a light source window provided at a light source side and a light receiving window provided at a light receiving element side for measuring said contamination in accordance with a transmittance of light through the optical path gap, said measuring means including a spacer ring having a plurality of projections each extending from said light source window to said light receiving window to cause said optical path to be less than substantially 0.34 mm.

2. A device for measuring contamination of a lubricant, comprising:

measuring means, dipped in said lubricant, for detecting an amount of contaminant in said lubricant;

temperature detecting means for detecting a lubricant temperature;

controlling means for generating a control signal in response to respective signals from said measuring means and said temperature detecting means; and signaling means for signaling a level of contamination in response to the control signal;

wherein said controlling means operates said signaling means when said temperature detecting means detects that the lubricant temperature has reached a predetermined temperature.

3. A device according to claim 2 for use with an engine to measure lubricant contamination therein, wherein said controlling means comprises holding means for holding a measurement value generated from said measuring means irrespective of whether said engine is running or stopped; signaling driving means for driving said signaling means in accordance with the measurement value held in said holding means during the operation of the engine; and updating means for updating the measurement value held in said holding means to a new value upon each measurement.

4. A device according to claim 2, wherein said temperature detecting means supplies a small forward bias current to a light-emitting diode so as to detect the lubricant temperature by means of a voltage drop generated across the light-emitting diode.

5. A device according to claim 2, wherein said signaling means comprises a plurality of indicators, and the amount of contaminant in the lubricant is indicated stepwise by the number of illuminated indicators.

6. Apparatus for measuring contamination in a lubricant, comprising a measuring device dipped in said lubricant, said measuring device including:

light source means for providing light;

a light source window adjacent said light source means;

light receiving means for receiving the light provided by said light source means and propagated through said lubricant a light receiving window adjacent said light receiving means and defining an optical gap path length with respect to said light source window; and spacer means having a plurality of projections each extending between said light source window and said light receiving window;

whereby a measure of said contamination corresponds to light transmittance through said optical gap path length.

7. Apparatus according to claim 6 wherein said spacer means projections extend between said light source window and said light receiving window so as to hold said optical path length to less than substantially 0.34 mm.

8. Apparatus according to claim 6 wherein each of said light source window and said light receiving window are substantially flat windows.

9. Apparatus according to claim 6 wherein said spacer means includes three projections.

10. Apparatus according to claim 9 wherein each of said three projections has a width which is less than substantially 0.34 mm.

11. Apparatus according to claim 6 wherein said spacer means includes:

a spacer ring mounted adjacent one of said light source window and said light receiving window; and a plurality of U-shaped projections coupled to said spacer ring and having one arm of each said U-shaped projection extending between said light source window and said light receiving window.

* * * * *

UNITED STATES PATENT AND TRADEMARK OFFICE
CERTIFICATE OF CORRECTION

PATENT NO. : 4,699,509

DATED : October 13, 1987

INVENTOR(S) : KAMIYA, et al.

It is certified that error appears in the above-identified patent and that said Letters Patent is hereby corrected as shown below:

Delete Fig. 2 and                         insert corrected Fig. 2

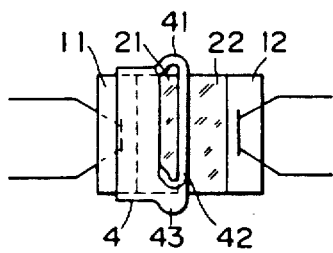

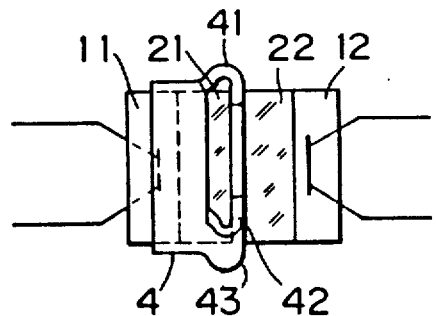

Signed and Sealed this

Fifth Day of April, 1988

Attest:

DONALD J. QUIGG

Attesting Officer     Commissioner of Patents and Trademarks